United States Patent
Kitano et al.

(10) Patent No.: US 10,312,841 B2
(45) Date of Patent: Jun. 4, 2019

(54) MOTOR DRIVE CONTROLLING APPARATUS, MOTOR DRIVE CONTROLLING METHOD, AND TUBE PUMP

(71) Applicant: MINEBEA MITSUMI Inc., Nagano (JP)

(72) Inventors: Takamichi Kitano, Shizuoka (JP); Hidetoshi Hijikata, Shizuoka (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 15/942,662

(22) Filed: Apr. 2, 2018

(65) Prior Publication Data
US 2018/0287527 A1    Oct. 4, 2018

(30) Foreign Application Priority Data
Apr. 3, 2017    (JP) ................. 2017-073556

(51) Int. Cl.
| G05B 11/01 | (2006.01) |
| H02P 6/22 | (2006.01) |
| F04B 49/02 | (2006.01) |
| F04B 49/20 | (2006.01) |
| F04B 51/00 | (2006.01) |

(Continued)

(52) U.S. Cl.
CPC ............ *H02P 6/22* (2013.01); *A61M 1/1039* (2014.02); *A61M 1/1046* (2013.01); *A61M 1/1086* (2013.01); *A61M 1/14* (2013.01); *F04B 43/1253* (2013.01); *F04B 49/02* (2013.01); *F04B 49/20* (2013.01); *F04B 51/00* (2013.01); *H02P 6/16* (2013.01); *H02P 29/024* (2013.01);

(Continued)

(58) Field of Classification Search
CPC .......................................................... H02P 6/22
USPC .......................................................... 318/628
See application file for complete search history.

(56) References Cited

U.S. PATENT DOCUMENTS

| 8,810,172 B2 | 8/2014 | Kozawa et al. |
| 2004/0066165 A1 | 4/2004 | Kamio et al. |

FOREIGN PATENT DOCUMENTS

| JP | 10-290831 A | 11/1998 |
| JP | 2011-142721 A | 7/2011 |

(Continued)

OTHER PUBLICATIONS

Extended European Search Report dated Aug. 29, 2018 for corresponding European Application No. 18165039.1.
(Continued)

*Primary Examiner* — Erick D Glass
(74) *Attorney, Agent, or Firm* — Pearne & Gordon LLP

(57) ABSTRACT

A motor drive controlling apparatus includes: a controller that outputs a drive control signal; a motor driver that generates and outputs a drive signal to a motor; and an encoder that detects a rotational position of the motor. The controller has a measurement unit that detects a time point when rotation of the motor is switched to a reverse direction of a target rotational direction by an external factor during input of the speed command signal, and measures a movement amount in the reverse direction from a rotational position of the motor at a time point of the switching, and a transmitting unit that transmits, to the motor driver, a switching signal that switches a conduction method from 180-degree conduction to 120-degree conduction in a case where the movement amount is a predetermined threshold or more.

8 Claims, 10 Drawing Sheets

(51) Int. Cl.
*F04B 43/12* (2006.01)
*H02P 6/16* (2016.01)
*A61M 1/10* (2006.01)
*A61M 1/14* (2006.01)
*H02P 29/024* (2016.01)

(52) U.S. Cl.
CPC ............... *A61M 2205/3317* (2013.01); *A61M 2205/3327* (2013.01); *A61M 2205/3365* (2013.01)

(56) References Cited

FOREIGN PATENT DOCUMENTS

| | | |
|---|---|---|
| JP | 2011-250663 A | 12/2011 |
| JP | 2015-204722 A | 11/2015 |

OTHER PUBLICATIONS

Japanese Office Action dated Oct. 16, 2018 for corresponding Japanese Application No. 2017-073556 and English translation.

MOTOR DRIVE CONTROLLING APPARATUS, MOTOR DRIVE CONTROLLING METHOD, AND TUBE PUMP

CROSS-REFERENCE TO RELATED APPLICATION

The present application claims priority to and incorporates by reference the entire contents of Japanese Patent Application No. 2017-073556 filed in Japan on Apr. 3, 2017.

BACKGROUND OF THE INVENTION

1. Field of the Invention

The present invention relates to a motor drive controlling apparatus, a motor drive controlling method, and a tube pump.

2. Description of the Related Art

Conventionally, there has been known a tube pump of related art as a pump apparatus. The tube pump delivers liquid contained in a tube by causing a motor to rotate rollers while pressing and flattening the tube. A tube pump is used in a medical apparatus, and there has been known a pump apparatus (blood pump) for artificial dialysis in which a brushless direct current (DC) motor rotates a rotor having rollers, for example.

There exist, for example, a 120-degree conduction method and a 180-degree conduction method among conduction methods of this brushless DC motor used in the tube pump. Commonly, this brushless DC motor to be operated in the 180-degree conduction method starts to rotate in the 120-degree conduction method, and switches to the low-noise and low-vibration 180-degree conduction method in accordance with an actual rotational speed of the motor. When an external factor causes the actual rotational speed of the motor to fall below a predetermined rotational speed, the conduction method is switched from the 180-degree conduction method to the 120-degree conduction method so as to sustain the control over of the motor (see Japanese Laid-open Patent Publication No. 10-290831).

However, a brushless DC motor that is used for a conventional tube pump needs some time to switch a conduction method from the 180-degree conduction method to the 120-degree conduction method. Then, there is a problem in that, in a case where a motor is reversed by an external factor before a conduction method is switched, as such reversal is detected, a protective operation (for example, a short brake) is added thereto until the motor is stopped or a reverse speed thereof is an extremely low speed that is regarded as stopping, so that it may be impossible to drive the motor until a reverse phenomenon is removed and the protective operation is released.

SUMMARY OF THE INVENTION

A motor drive controlling apparatus includes: a controller, a motor driver, and a position detector. The controller generates and outputs a drive control signal in response to an input of a speed command signal and a rotational direction signal. The motor driver generates a drive signal and outputs the generated drive signal to a motor, in response to an input of the drive control signal. The position detector that detects a rotational position of the motor and outputs a detection signal that is based on a detection result. The motor driver provides 120-degree conduction as a conduction method from a start of rotation of the motor to a predetermined rotational speed or provides 180-degree conduction as a conduction method for the predetermined rotational speed or more. The controller has: a measurement unit that detects a time point when rotation of the motor is switched to a reverse direction of a target rotational direction that is based on the rotational direction signal by an external factor during input of the speed command signal, based on the detection signal, and measures a movement amount in the reverse direction from a rotational position of the motor at a time point of the switching, based on the detection signal; and a transmitting unit that transmits, to the motor driver, a switching signal that switches a conduction method for the motor driver from the 180-degree conduction to the 120-degree conduction in a case where the movement amount is a predetermined threshold or more.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
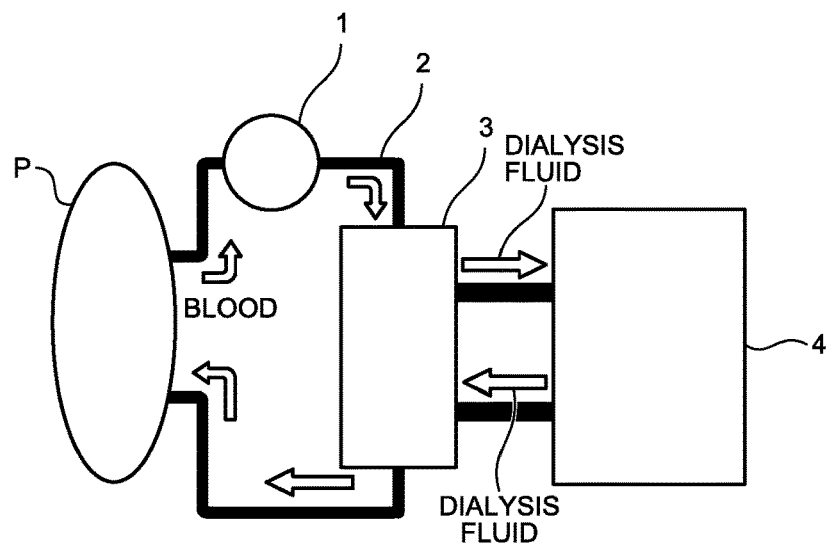
FIG. 1 is a diagram illustrating a configuration example of an artificial dialysis system that assembles a blood pump according to an embodiment.

Hereinafter, a motor drive controlling apparatus, a motor drive controlling method, and a tube pump according to an embodiment will be described with reference to the drawings. Additionally, a relationship between numerical values of respective elements, scales of respective elements, or the like in the drawings may be different from actual ones.

Furthermore, the drawings may include parts where relationships between mutual numerical values or scales are different from one another.

Embodiment

Hereinafter, a case will be described where a tube pump that uses a motor drive controlling apparatus according to an embodiment is a blood pump of an artificial dialysis system. FIG. 1 is a diagram illustrating a configuration example of an artificial dialysis system that assembles a blood pump according to an embodiment.

The artificial dialysis system as illustrated in FIG. 1 has a blood pump 1 (one example of tube pump), a dialyzer 3, and a dialysis fluid supplier 4. The blood pump 1 delivers blood of a patient P to the dialyzer 3 through a tube 2 (blood removal).

Such a dialyzer 3 executes a process of removing wastes, maintaining electrolytes, and maintaining a water amount for blood of such a patient P due to a semipermeable membrane and a dialysis fluid that is supplied from the dialysis fluid supplier 4. Furthermore, the blood pump 1 returns blood that is processed by the dialyzer 3 to such a patient P through the tube 2 (blood return).

Figure 2:
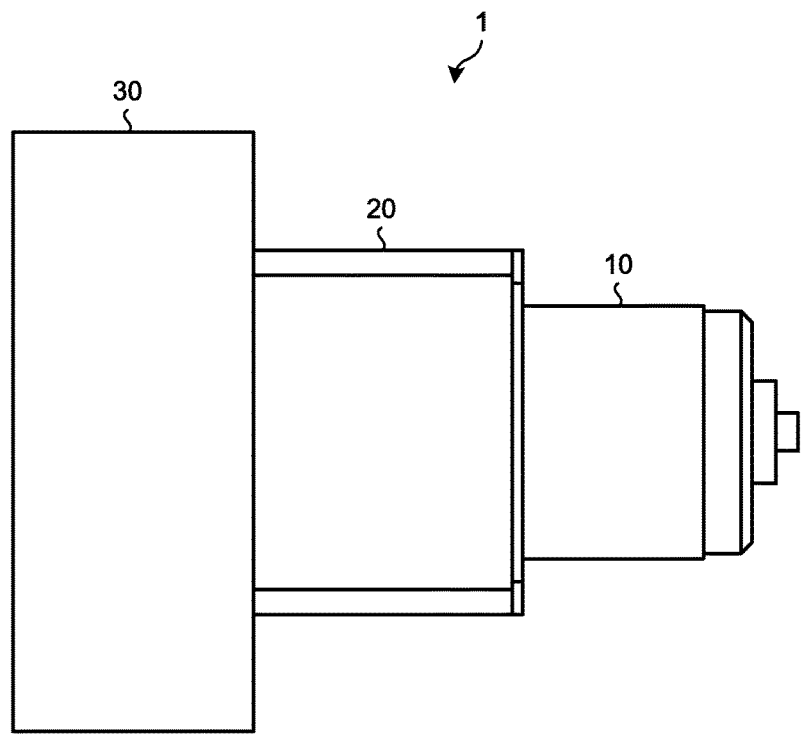
FIG. 2 is a first diagram for illustrating a blood pump as illustrated in FIG. 1.
Figure 3:
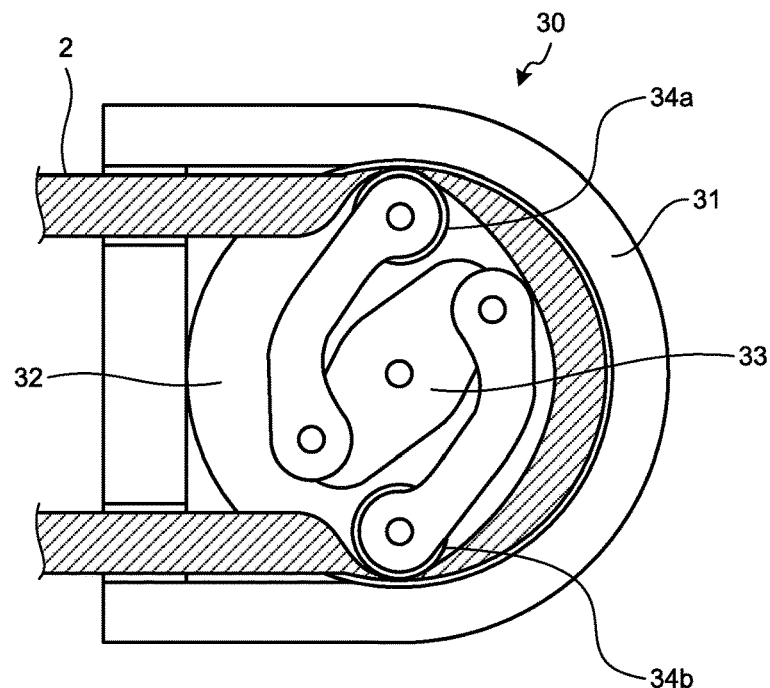
FIG. 3 is a second diagram for illustrating a blood pump as illustrated in FIG. 1.

FIG. 2 and FIG. 3 are diagrams for illustrating the blood pump 1 as illustrated in FIG. 1. As illustrated in FIG. 2, the blood pump 1 has a motor device 10, a speed reducer 20, and a pump system 30. Additionally, FIG. 2 is a diagram of the blood pump 1 as illustrated in FIG. 1 that is viewed from a side surface side and FIG. 3 is a diagram of the blood pump 1 as illustrated in FIG. 1 that is viewed from a side facing a pump system 30.

In FIG. 2, the motor device 10 is a drive source that supplies rotational drive force to a rotor 32 (see FIG. 3) of the pump system 30 through the speed reducer 20 and assembles a motor 11 (see FIG. 6) as described later. The speed reducer 20 is connected to a rotating shaft of the motor device 10 (motor 11) and reduces a rotational speed of the motor 11 with a predetermined reduction ratio. The pump system 30 is connected to a rotating shaft (output shaft) of the speed reducer 20.

The pump system 30 has a housing 31, a rotor 32, a roller support 33, a roller 34a, and a roller 34b as illustrated in FIG. 3. The housing 31 forms an internal space for accommodating the tube 2 and the rotor 32. The tube 2 is arranged or provided along an arc-shaped inner circumferential wall surface that is possessed by the housing 31. The rotor 32 is connected to a rotating shaft (output shaft) of the speed reducer 20.

The roller support 33 is connected to the rotor 32 and rotates with rotation of the rotor 32. The roller 34a and the roller 34b are attached to both ends of the roller support 33, respectively. The roller support 33 rotatably supports the roller 34a and the roller 34b that press the tube 2.

The roller 34a and the roller 34b rotate with rotation of the roller support 33. That is, the roller 34a and the roller 34b rotate when driven by the motor device 10 (motor 11) to press the tube 2 that is arranged or provided along an inner circumferential wall surface of the housing 31 and deliver the liquid (blood) in the tube 2.

Figure 4:
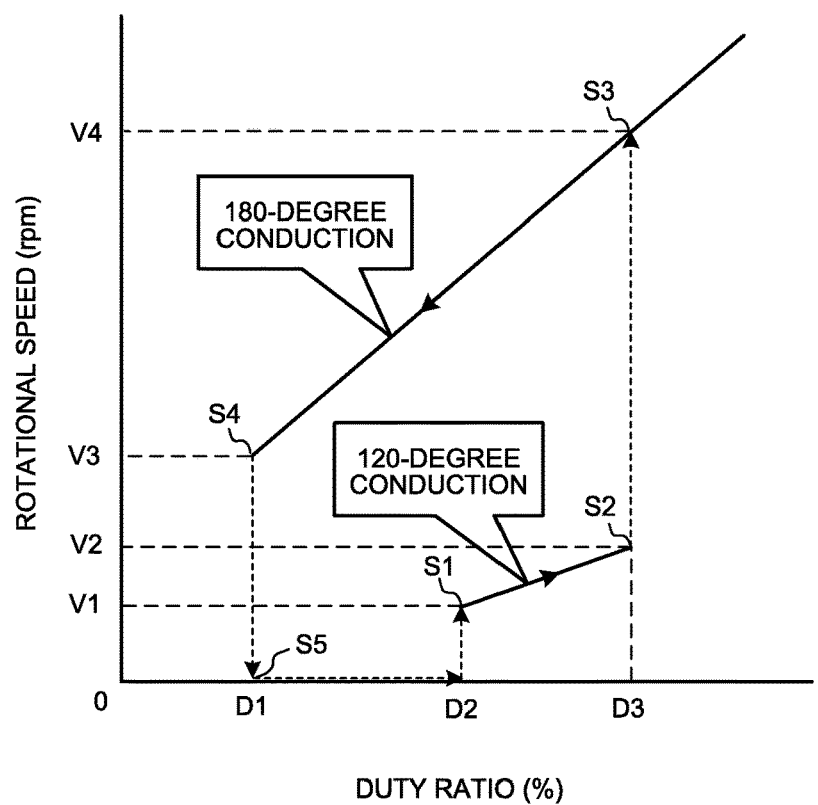
FIG. 4 is a diagram for illustrating an example of a switching operation for a conduction method in a motor device according to an embodiment.

FIG. 4 is a diagram for illustrating an example of a switching operation for a conduction method in the motor device 10 according to an embodiment. As illustrated in FIG. 4, a 120-degree conduction method (that will also be called 120-degree conduction below) and the 180-degree conduction method (that will also be called 180-degree conduction below) are provided as conduction methods for the motor 11 in the motor device 10.

120-degree conduction is a conduction method that is used as the motor 11 is driven at a low rotational speed (for example, V1–V2 rpm). 180-degree conduction is a conduction method that is used as the motor 11 is driven at a medium or high rotational speed (for example, V3 rpm or more). In the following embodiment, a case where V1–V2 rpm is less than 100 rpm and V3 rpm is more than 100 rpm will be described as an example.

120-degree conduction has an advantage of a large torque at a low rotational speed while having a disadvantage of large noise and vibration at a medium or high rotational speed. On the other hand, 180-degree conduction has a disadvantage of a small torque at a low rotational speed as compared with 120-degree conduction while having an advantage of small noise and vibration at a medium or high rotational speed.

Hence, in an embodiment, control is executed in such a manner that conduction is 120-degree conduction at a time of restarting of the motor 11 and is switched to 180-degree conduction as an actual rotational speed is a predetermined rotational speed (for example, V2 rpm) or more.

Furthermore, in an example as illustrated in FIG. 4, the following control is executed in a case where the motor 11 rotates at a low rotational speed (for example, 100 rpm). First, as a Pulse Width Modulation (PWM) duty ratio (that will also be called a duty ratio below) of the motor 11 is increased by 120-degree conduction, rotation of the motor 11 starts at D2% and a rotational speed thereof is V1 rpm (step S1).

Subsequently, as the duty ratio is increased and a rotational speed is V2 rpm or more at D3% (step S2), a conduction method is switched from 120-degree conduction to 180-degree conduction (step S3). Accordingly, a rotational speed of the motor 11 rapidly increases from V2 rpm to V4 rpm and exceeds a target rotational speed (100 rpm).

Then, as a duty ratio is decreased while keeping 180-degree conduction, a rotational speed is V3 rpm at D1% (step S4). Subsequently, as a duty ratio is decreased, a rotational speed is reduced in a free state where the motor 11 is not capable of rotating due to a lack of torque, and as a rotational speed is V2 rpm or less, a conduction method is switched from 180-degree conduction to 120-degree conduction (step S5).

Then, as a rotational speed is 100 rpm or less, a duty ratio increases but a free state where the motor 11 is not capable of rotating continues (Steps S4 to S5 and Steps S5 to S1), and the motor 11 restarts rotation with 120-degree conduction at D2% again (step S1). Thus, the motor 11 repeats steps of 120-degree conduction (Steps S1 to S2), 180-degree conduction (Steps S3 to S4), and free one (Steps S4 to S5 and Steps S5 to S1), so that it is possible for an average of a rotational speed of the motor 11 to be a target rotational speed (100 rpm).

Additionally, the motor 11 in an embodiment is used to be further decelerated by the speed reducer 20 as described above, and hence, the above-mentioned steps are repeated so that there is not a problem in practice even in a case where a rotational speed varies microscopically.

Figure 5:
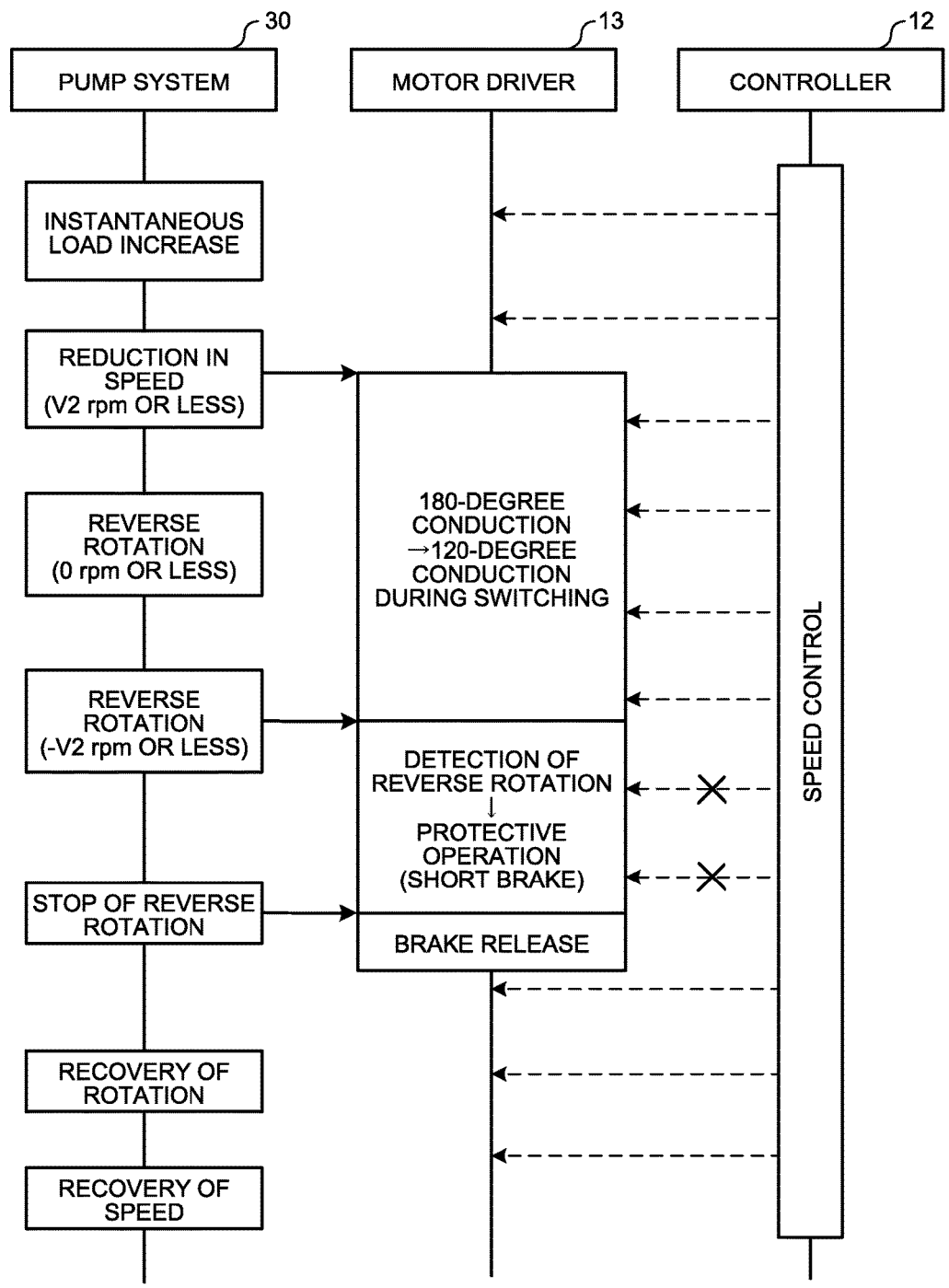
FIG. 5 is a diagram illustrating a process flow for a motor drive controlling apparatus in a reference example.

Next, a problem in such a motor device 10 will be described with reference to FIG. 5. FIG. 5 is a diagram illustrating a process flow for a motor drive controlling apparatus in a reference example.

As illustrated in FIG. 5, a motor driver 13 (see FIG. 6) outputs a drive signal to a motor 11 (see FIG. 6) to drive the motor 11. Such a drive signal is generated based on the 120-degree conduction method or the 180-degree conduction method in the motor driver 13 and output to the motor 11.

A controller 12 (see FIG. 6) outputs a drive control signal to the motor driver 13 to execute a variety of control of the motor driver 13. For example, a speed command is transmitted to the motor driver 13 based on a speed command signal that is a command from a user and an encoder signal (see FIG. 6) that is output from an encoder 14 to control a rotational speed of the motor 11.

Herein, in a case where a load that is caused by an external factor instantaneously increases for the pump system 30 during a low speed operation and a rotational speed of the motor 11 is less than a predetermined rotational speed (for example, V2 rpm), the motor driver 13 starts an operation to switch a conduction method from 180-degree conduction to 120-degree conduction as described above.

However, as the load continues to be added before the conduction method is switched to 120-degree conduction and the motor 11 rotates in a direction opposite to a target rotational direction (0 rpm or less) (that will also be called reverse rotation below) and further such reverse rotation is of a predetermined rotational speed (for example, −V2 rpm) or less, the motor driver 13 detects it and then the motor driver 13 starts a protective operation to protect the motor 11.

That is because, as the motor 11 reversely rotates with the 180-degree conduction method that generates a drive waveform of a sine wave based on a previous signal from a hall element 15 (see FIG. 6; an example of a magnetic sensor), an order of conduction that is different from previous one is detected, and therefore, it may be impossible to generate a drive waveform. Additionally, it is possible for the motor driver 13 to detect a rotational speed of the motor 11 due to the hall element 15 that is assembled in the motor device 10.

A protective operation to protect the motor 11 is, for example, a short brake that stops rotation of the motor 11. Then, as rotation of the motor 11 is stopped or is at an extremely low speed that is regarded as stopping due to such a protective operation, the protective operation is released so that rotation of the motor 11 is recovered. On the other hand, even in a case where the controller 12 provides a speed command to the motor driver 13 during a protective operation that is executed by such a motor driver 13, it may be impossible to drive the motor device 10.

Hence, the controller 12 in a motor drive controlling apparatus according to an embodiment is provided to have a configuration that will be described below, so that it is possible to drive the motor 11 continuously even in a case where the motor 11 is reversed by an external factor before a conduction method is switched from the 180-degree conduction method to the 120-degree conduction method.

Figure 6:
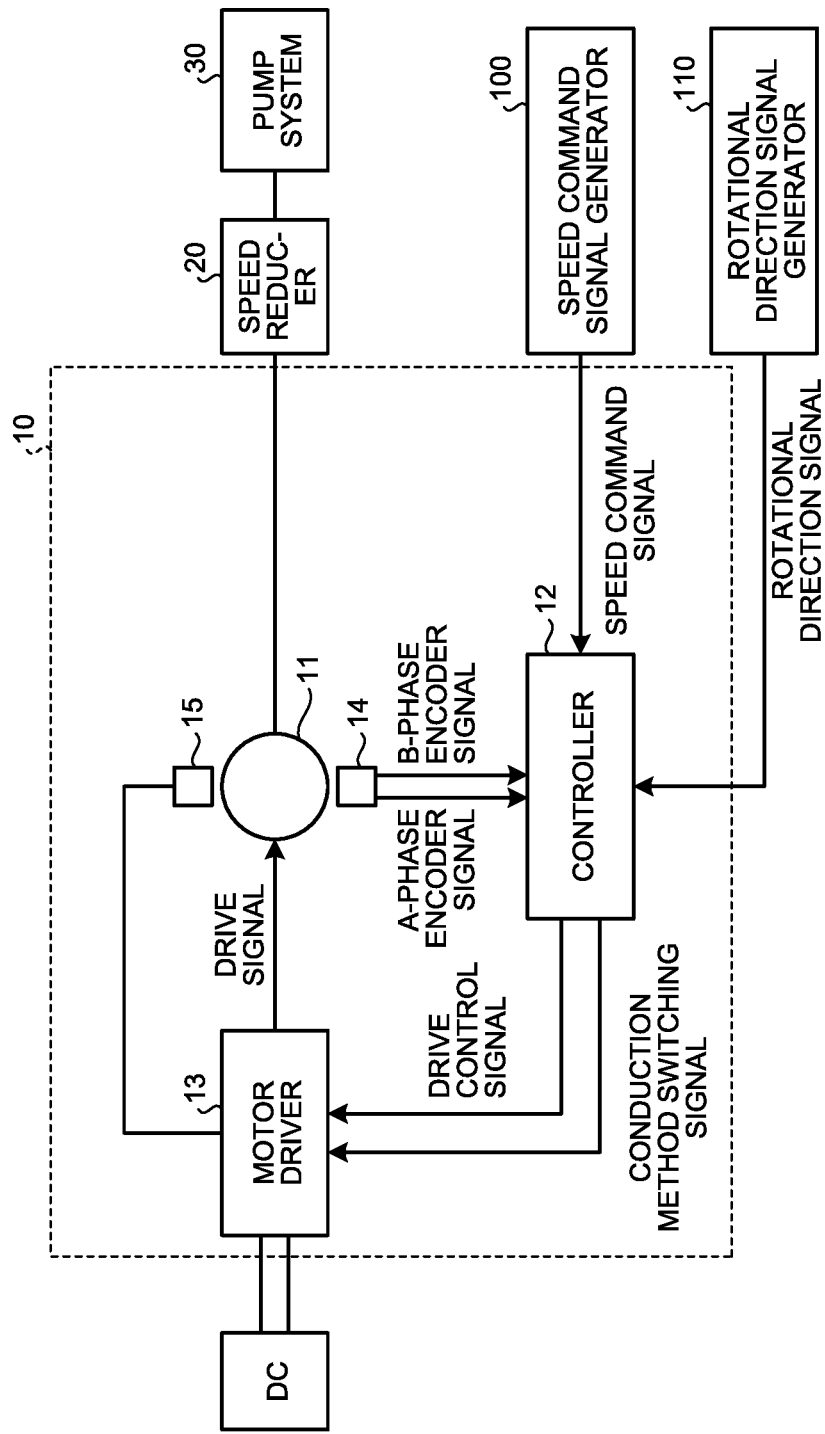
FIG. 6 is a block diagram illustrating a configuration example of a motor device as illustrated in FIG. 2.

FIG. 6 is a block diagram illustrating a configuration example of the motor device 10 as illustrated in FIG. 2. As illustrated in FIG. 6, the motor device 10 has a motor 11, a controller 12, a motor driver 13, an encoder 14 (an example of a position detector), and a hall element 15 (an example of a magnetic sensor).

The motor 11 is connected to the pump system 30 through the speed reducer 20. The motor 11 is, for example, a three-phase brushless DC motor. The motor 11 is driven and controlled by a motor drive controlling apparatus that includes the controller 12 and the motor driver 13. Additionally, a motor drive controlling apparatus may include the encoder 14 and the hall element 15.

The controller 12 is connected to a speed command signal generator 100 and a rotational direction signal generator 110 that are external devices. The controller 12 is composed of, for example, a microprocessor (Micro-Processing Unit: MPU). A speed command signal from the speed command signal generator 100 is input to the controller 12 and further a rotational direction signal from the rotational direction signal generator 110 is input thereto, so that a drive control signal is generated based on such a speed command signal and a rotational direction signal.

Such a speed command signal is a signal that is generated by the speed command signal generator 100 and command information that specifies a target rotational speed of the motor 11. Specifically, a speed command signal is a pulsed signal where a count number is a target rotational step number and a count number per unit time is a target rotational speed.

The speed command signal generator 100 generates, and outputs to the controller 12, a clock signal with a frequency dependent on a target rotational speed as a speed command signal due to, for example, a Pulse Frequency Modulation (PFM).

Furthermore, a rotational direction signal from the rotational direction signal generator 110 is input to the controller 12, so that a rotational direction of the motor 11 is controlled based on such a rotational direction signal. A rotational direction signal is command information that specifies a target rotational direction (that will also be called a "normal direction") of the motor 11. Specifically, a rotational direction signal is a digital signal with a value that is different between a case where a target rotational direction is a clockwise (CW) direction and a case where it is a counterclockwise (CCW) direction.

Then, the controller 12 generates, as a drive control signal, a pulse width modulation (PWM) signal for rotating the motor 11 at a rotational speed that corresponds to a clock signal due to, for example, PWM. Additionally, such a drive control signal includes a control signal for rotating the motor 11 in a rotational direction that is based on a rotational direction signal, as well as a PWM signal.

The motor driver 13 is connected to a direct-current power source DC and generates, and outputs to the motor 11, a drive signal due to input of a drive control signal that is generated by the controller 12. The motor driver 13 has, for example, an inverter circuit and a pre-drive circuit that is an analogue integrated circuit.

An inverter circuit outputs a drive signal to the motor 11 based on an output signal that is output from a pre-drive circuit and executes conduction for three armature coils that are included by the motor 11. An inverter circuit is configured, for example, in such a manner that pairs of series circuits of two switch elements that are provided on both ends of the direct current power source DC are arranged for respective phases (a U-phase, a V-phase, and a W-phase) of three armature coils, respectively. Then, in each pair of such two switch elements, a terminal for each phase of the motor 11 is connected to a connection point between both switch elements.

A pre-drive circuit generates, and outputs to an inverter circuit, an output signal for driving the inverter circuit based on a drive control signal that is input from the controller 12. Such an output signal is, for example, six kinds of switching signals that correspond to respective switch elements of an inverter circuit. Such output signals are output to an inverter circuit, so that a switch element that corresponds to each output signal executes an on/off operation and a drive signal is output to the motor 11, so as to supply electric power to each phase for the motor 11.

Additionally, a switching signal that is output to an inverter circuit is output at timing that is mutually different between the 120-degree conduction method and the 180-degree conduction method. Therefore, in an embodiment, a conduction method for the motor 11 is controlled in a pre-drive circuit of the motor driver 13.

The encoder 14 is an example of a position detector that detects a rotational position of the motor 11 (rotor 32). The encoder 14 outputs a pulsed signal dependent on a speed command signal (clock signal) and outputs, to the controller 12, a detection signal (encoder signal) that is based on a count number of such a pulsed signal.

The encoder 14 alternately outputs a signal from an A-phase and a signal from a B-phase with a phase difference from such an A-phase being approximately 90 degrees, respectively, in a case where the motor 11 rotates. A measurement unit 41 (see FIG. 7) that is included by the controller 12 counts, due to a counter, a rise/fall state change of an output waveform for an A-phase and a rise/fall state change of an output waveform for a B-phase, so that a rotational step number, a rotational direction, and a rotational speed are measured in practice.

The hall element 15 is an example of a magnetic sensor that detects a position of a magnetic pole in the motor 11 (rotor 32) and outputs a positional signal (hall signal) that is based on a result of such detection to a pre-drive circuit of the motor driver 13. A pre-drive circuit adjusts timing when an on/off operation of each switch element of an inverter circuit is switched, based on a received hall signal.

Furthermore, a pre-drive circuit detects a rotational speed of the motor 11 based on a state change of a received hall signal and switches a conduction method for the motor 11. Additionally, a hall integrated circuit (hall IC) may be used instead of the hall element 15.

The controller 12 generates, and outputs to the motor driver 13, a drive control signal (PWM signal) based on a speed command signal (clock signal) and an encoder signal that is output by the encoder 14. The controller 12 compares a count number of a clock signal (target rotational step number) and a count number of an encoder signal (actual rotational step number) while the motor 11 rotates, due to, for example, input of the clock signal.

Then, after a ratio between count numbers of a clock signal and an encoder signal is adjusted, the controller 12 generates, and outputs to the motor driver 13, in a case where both count numbers are different, a PWM signal with a changed duty ratio in such a manner that both count numbers equal to each other. Additionally, the controller 12 may execute control to maintain a rotational speed of the motor 11 by using a signal that is output by the hall element 15, instead of an encoder signal that is output by the encoder 14, while the motor 11 rotates due to input of a clock signal.

Meanwhile, in the motor device 10, the above-mentioned protective function that protects the motor 11 in a case where the motor 11 is reversely rotated by a load that is caused by an external factor is provided to a pre-drive circuit of the motor driver 13. A pre-drive circuit detects an actual rotational direction and rotational speed of the motor 11 based on a hall signal transmitted from the hall element 15.

Then, in a case where detection is executed based on a hall signal in such a manner that the motor 11 rotates in a rotational direction (that will also be called a reverse direction below) opposite to a target rotational direction and further rotation in the reverse direction is of a predetermined rotational speed or more (that is, rotation in a normal direction is of a predetermined minus rotational speed or less), a pre-drive circuit executes a protective operation that protects the motor 11.

Herein, in an embodiment, in a case where the controller 12 detects rotation of the motor 11 in a reverse direction due to an encoder signal from the encoder 14, the controller 12 outputs, to the motor driver 13, a conduction method switching signal that forcibly restarts the motor driver 13 with the 120-degree conduction method, before the above-mentioned protective operation is executed.

Thereby, it is possible to prevent the motor 11 from starting a protective operation even in a case where the motor 11 is reversed by an external factor before a conduction method is switched from the 180-degree conduction method to the 120-degree conduction method. Therefore, according to an embodiment, it is possible to drive the motor 11 continuously.

Furthermore, in an embodiment, a resolution of the encoder 14 is higher than a resolution of the hall element 15. Thereby, it is possible for the controller 12 to detect rotation of the motor 11 in a reverse direction rapidly based on an encoder signal from the encoder 14 before the motor driver 13 starts a protective operation based on a hall signal transmitted from the hall element 15.

Figure 7:
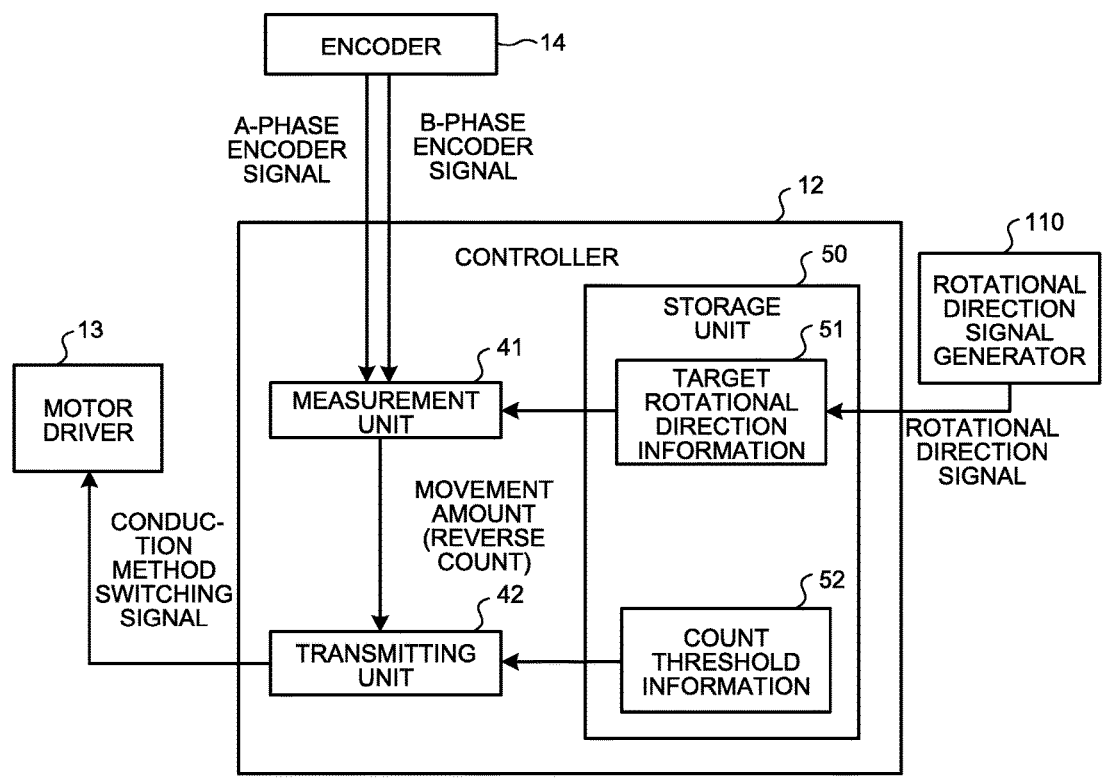
FIG. 7 is a block diagram illustrating a configuration example of a controller according to an embodiment.

FIG. 7 is a block diagram illustrating a configuration example of the controller 12 according to an embodiment. The controller 12 has a measurement unit 41, a transmitting unit 42, and a storage unit 50. The storage unit 50 stores target rotational direction information 51 and count threshold information 52. Additionally, the transmitting unit 42 includes a timer.

As described in detail below, the measurement unit 41 detects, based on an encoder signal (detection signal), a time point when rotation of the motor 11 is switched to a reverse direction of a target rotational direction that is based on a rotational direction signal from the rotational direction signal generator 110, by an external factor, during input of a speed command signal from the speed command signal generator 100, and measures a movement amount in the reverse direction from a rotational position of the motor 11 at a time of switching, based on the encoder signal. Then, in a case where a movement amount is a predetermined threshold or more, the transmitting unit 42 transmits, to the motor driver 13, a switching signal that switches a conduction method for the motor driver 13 from 180-degree conduction to 120-degree conduction. Additionally, the measurement unit 41 counts a count value that corresponds to a movement amount of the motor 11 in a reverse direction and the transmitting unit 42 transmits a switching signal to the motor driver 13 in a case where a count value is a specified value.

The storage unit 50 receives a rotational direction signal from the rotational direction signal generator 110 and stores target rotational direction information 51 that is information on a target rotational direction (CW direction or CCW direction) of the motor 11. The measurement unit 41 measures a reverse count that counts a movement amount of the motor 11 in a reverse direction, based on such target rotational direction information 51 and an A-phase encoder signal and a B-phase encoder signal from the encoder 14. A measurement method for such a reverse count will be described later.

The transmitting unit 42 compares a reverse count that is measured by the measurement unit 41 and a count threshold (an example of a specified value) that is stored in the count threshold information 52 of the storage unit 50. Additionally, such a count threshold is an example of a predetermined threshold for a movement amount of the motor 11 in a reverse direction. Then, in a case where a reverse count is a count threshold or more, the transmitting unit 42 transmits the above-mentioned conduction method switching signal (an example of a switching signal) to the motor driver 13.

Figure 8:
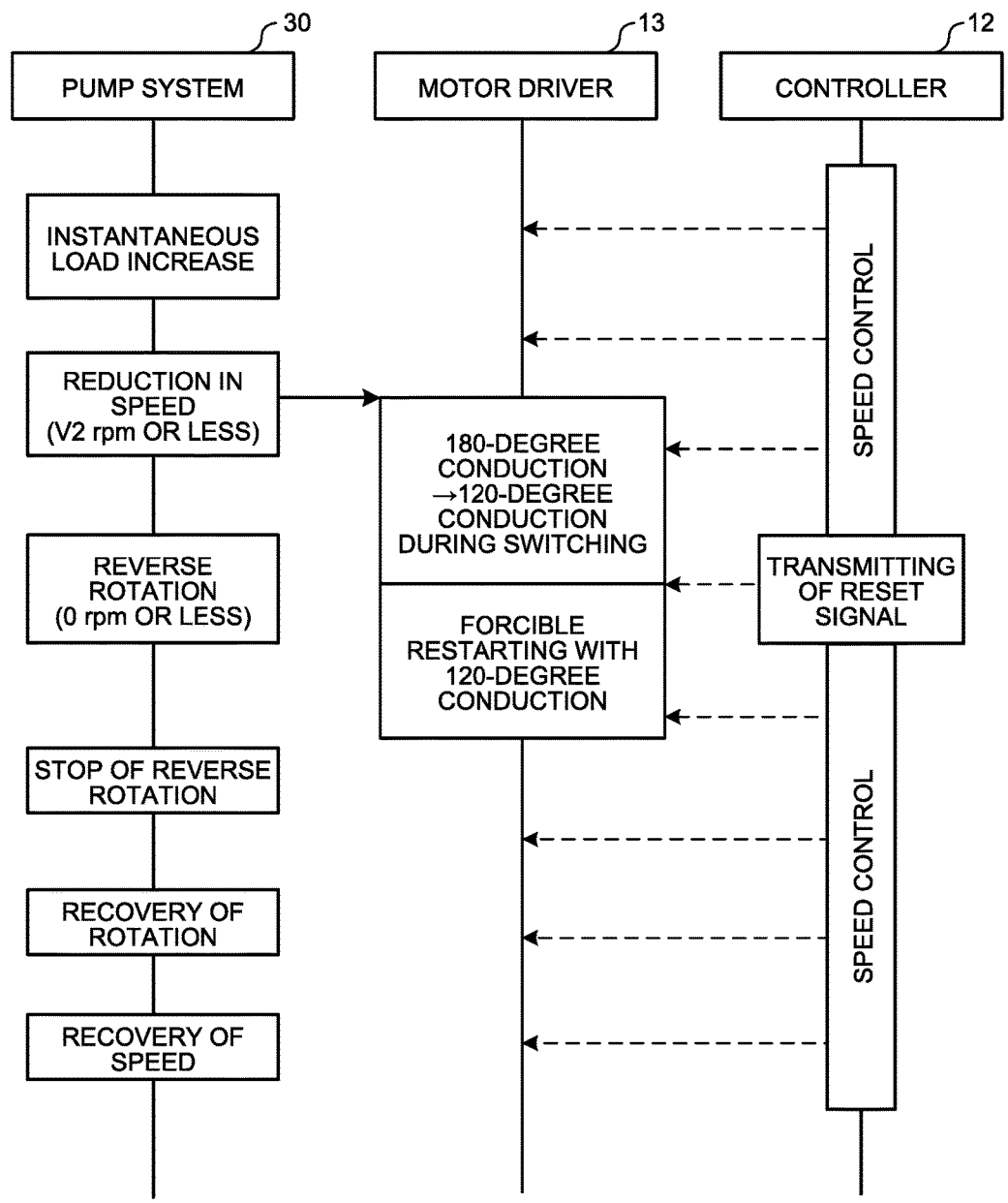
FIG. 8 is a diagram illustrating a process flow for a motor drive controlling apparatus according to an embodiment.

FIG. 8 is a diagram illustrating a process flow for a motor drive controlling apparatus according to an embodiment. As illustrated in FIG. 8, in a case where a load that is caused by an external factor instantaneously increases in the pump system 30 during a low speed operation and a rotational speed of the motor 11 is less than a predetermined rotational speed (for example, V2 rpm), the motor driver 13 starts an operation to switch a conduction method from 180-degree conduction to 120-degree conduction.

Herein, in an embodiment, as the motor 11 reversely rotates (that is, 0 rpm or less) and the controller 12 detects such reverse rotation, the controller 12 transmits a reset signal (an example of a switching signal) to the motor driver 13. Then, the motor driver 13 is forcibly restarted with 120-degree conduction by such a reset signal, so that it is possible to stop reverse rotation of the motor 11 without starting a protective operation and recover rotation in a normal direction (that will also be called normal rotation below).

Figure 9:
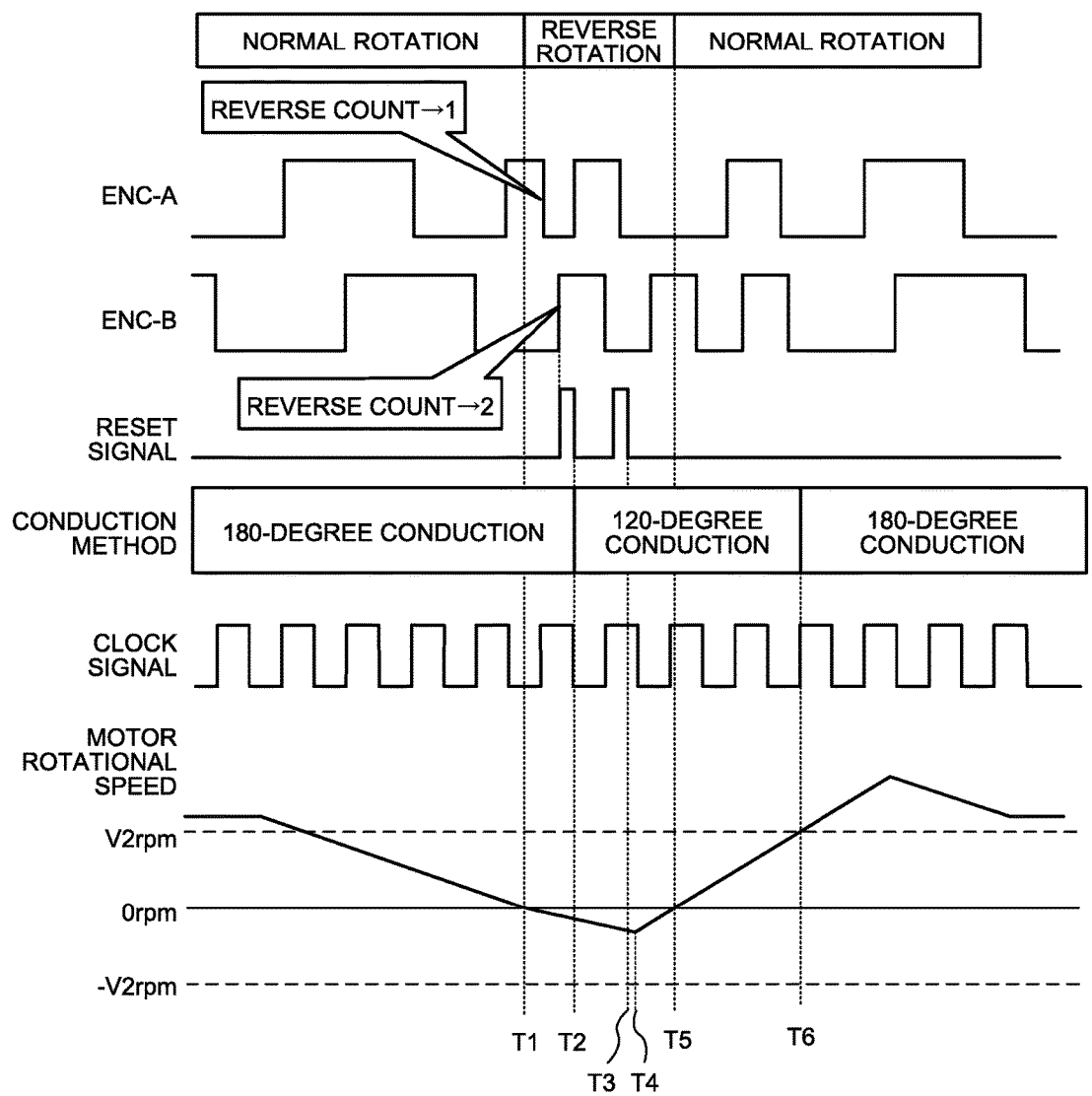
FIG. 9 is a timing diagram illustrating an example of a relationship between respective signal elements in a motor drive controlling apparatus according to an embodiment.

FIG. 9 is a timing diagram illustrating an example of a relationship between respective signal elements in a motor drive controlling apparatus according to an embodiment. Additionally, in an example as illustrated in FIG. 9, a case is indicated where a target rotational direction that is a command for the motor 11 due to a rotational direction signal is a CCW direction.

Therefore, as illustrated in FIG. 9, "0" (Low signal) is first output as a value of a B-phase encoder signal (ENC-B), "1" (High signal) is then output as a value of an A-phase encoder signal (ENC-A), and "1" is then output as a value of the B-phase encoder signal. Subsequently, "0" is output as a value of an A-phase encoder signal, and afterward, the A-phase encoder signal and a B-phase encoder signal are respectively and alternately output in such a predetermined order.

Additionally, in a case where a target rotational direction of the motor 11 is a CW direction, "0" is first output as a value of an A-phase encoder signal, "1" is then output as a value of a B-phase encoder signal, and "1" is then output as a value of the A-phase encoder signal. Subsequently, "0" is output as a value of a B-phase encoder signal, and afterward, an A-phase encoder signal and the B-phase encoder signal are respectively and alternately output in such a predetermined order.

Then, in a case where the motor 11 maintains a predetermined rotational speed, encoder signals that are output respectively and alternatively (an A-phase encoder signal and a B-phase encoder signal) are output depending on a speed command signal (clock signal). Furthermore, in an example as illustrated in FIG. 9, the motor 11 is herein driven with the 180-degree conduction method.

However, as a load that is caused by an external factor increases so that a rotational speed of the motor 11 is lower than a target rotational speed, an encoder signal that is output from the encoder 14 is delayed with respect to a clock signal. Moreover, as the motor 11 is reversed at a time T1, an encoder signal is output in an order that is different from a predetermined one.

In an example as illustrated in FIG. 9, as the motor 11 is reversed after a value "1" of an A-phase encoder signal is output, a value "1" of a B-phase encoder signal that is in a next order is not output but a value "0" of the A-phase encoder signal is output. Thus, as an encoder signal with an order that is different from a predetermined one is output, the measurement unit 41 of the controller 12 adds one count to a reverse count so as to change the reverse count from "0" to "1".

Moreover, as reverse rotation of the motor 11 is continued, a value "1" of a B-phase encoder signal that indicates that reverse rotation is continued is output after a value "0" of an A-phase encoder signal is output. Accordingly, the measurement unit 41 of the controller 12 further adds one count to a reverse count so as to change the reverse count from "1" to "2". Additionally, a specific count method for a reverse count in the measurement unit 41 will be described later.

Herein, in a case where a count threshold that is stored in the storage unit 50 is set at "2", the transmitting unit 42 of the controller 12 transmits a reset signal to the motor driver 13 as a reverse count is "2". Thereby, the motor driver 13 is forcibly restarted at time T2 and a conduction method is switched from the 180-degree conduction method to the 120-degree conduction method.

That is, due to such a reset signal, it is possible to drive the motor 11 continuously without restarting a protective operation that is executed by the motor driver 13. Such a reset signal is intermittently transmitted for a predetermined period of time (for example, until time T3). Additionally, a specific transmission method for such a reset signal will be described later.

Then, in an example as illustrated in FIG. 9, an increase in a rotational speed in a reverse direction is stopped at time T4 and the motor 11 is reversed from reverse rotation to normal rotation at time T5 to recover the normal rotation. Herein, in an embodiment, in a case where the measurement unit 41 detects that the motor 11 returns to a target rotational direction, the transmitting unit 42 stops transmitting of a reset signal.

Moreover, as a rotational speed of the motor 11 is a predetermined rotational speed or more at time T6, the motor driver 13 switches a conduction method from the 120-degree conduction method to the 180-degree conduction method. Such a predetermined rotational speed is, for example, V2 rpm in an example as illustrated in FIG. 9.

Additionally, a case where a count threshold is set at "2" has been indicated in an embodiment as described above, a setting value of a count threshold is "2" or more. For example, in a case where a count threshold is set at "2", a rotational direction fluctuates as the motor 11 rotates at an extremely low speed, that is, a so-called chattering phenomenon occurs, and it is possible to prevent sensitive forcible starting of the motor driver 13 even if a reverse count is "1".

Figure 10:
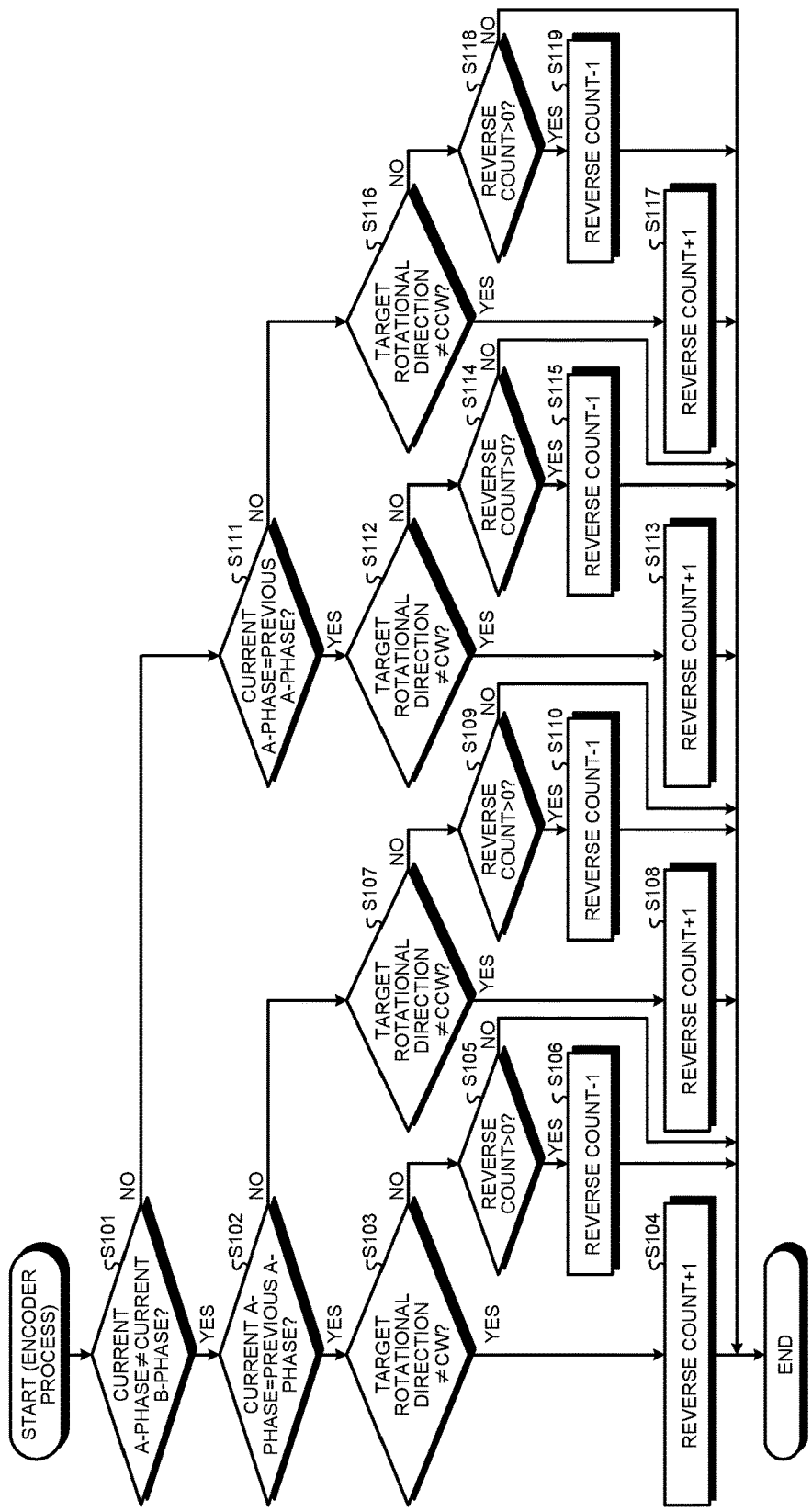
FIG. 10 is flowchart illustrating a measurement process for a reverse count according to an embodiment.
Figure 11:
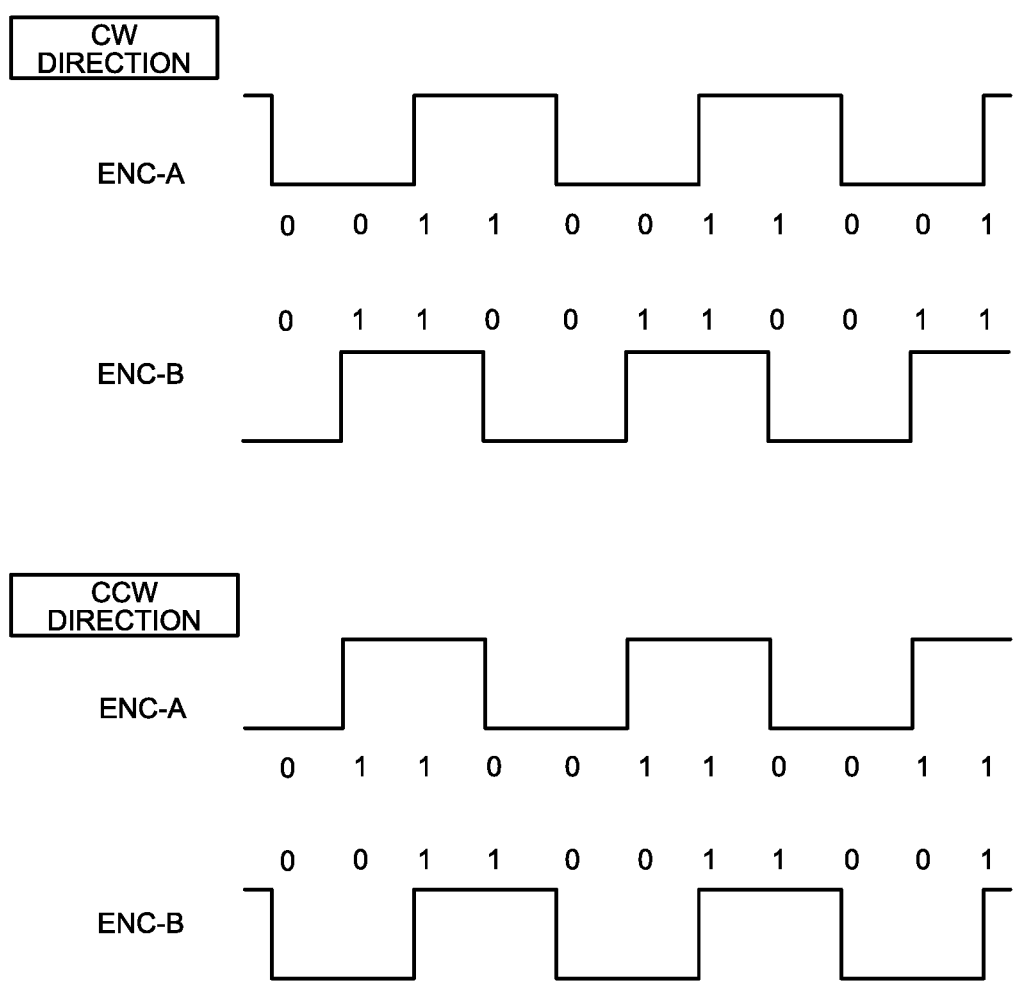
FIG. 11 is a schematic diagram illustrating output states of an encoder signal in a CW direction and a CCW direction according to an embodiment.

Subsequently, a measurement process for a reverse count will be described by using FIG. 10 and FIG. 11. FIG. 10 is a flowchart illustrating a measurement process for a reverse count according to an embodiment and FIG. 11 is a schematic diagram illustrating output states of an encoder signal in a CW direction and a CCW direction according to an embodiment. Additionally, a measurement process for a reverse count as illustrated in FIG. 10 is executed every time the measurement unit 41 receives a state change of an A-phase encoder signal or a B-phase encoder signal.

As illustrated in FIG. 10, the measurement unit 41 first determines whether a current value of an A-phase encoder signal is different from a current value of a B-phase encoder signal, that is, whether or not the current value of the A-phase encoder signal is "1" and the current value of the B-phase encoder signal is "0" or the current value of the A-phase encoder signal is "0" and the current value of the B-phase encoder signal is "1" (step S101), and in a case where such a condition is met (step S101, Yes), whether the current value of the A-phase encoder signal is equal to a value of the A-phase encoder signal at a time of a previous process is determined (step S102).

Subsequently, the measurement unit 41 determines, in a case where a current value of an A-phase encoder signal is equal to a value of the A-phase encoder signal at a time of a previous process (step S102, Yes), whether or not a target rotational direction is not a CW direction based on the target rotational direction information 51 (step S103). Then, in a case where a target rotational direction is not a CW direction (step S103, Yes), 1 is added to a reverse count (step S104) and such a process is ended.

That is, in a case of "step S101, Yes" and "step S102, Yes", a rotational direction of the motor 11 is a CW direction as illustrated in FIG. 11. Then, in a case of "step S103, Yes", a target rotational direction is a CCW direction, so that 1 is added to a reverse count.

Additionally, in a case where a determination condition at step S103 is not satisfied (step S103, No), that is, in a case where a rotational direction of the motor 11 is a CW direction that is equal to a target rotational direction, the measurement unit 41 determines whether or not a reverse count is more than 0 (step S105). Herein, in a case where a reverse count is more than 0 (step S105, Yes), 1 is subtracted from the reverse count (step S106) and such a process is ended, or otherwise (step S105, No), such a process is ended with no change.

Furthermore, in a case where a determination condition at step S102 is not satisfied (step S102, No), the measurement unit 41 determines whether or not a target rotational direction is not a CCW direction based on the target rotational direction information 51 (step S107). Then, in a case where a target rotational direction is not a CCW direction (step S107, Yes), 1 is added to a reverse count (step S108) and such a process is ended.

That is, in a case of "step S101, Yes" and "step S102, No", a rotational direction of the motor 11 is a CCW direction as illustrated in FIG. 11. Then, in a case of "step S107, Yes", a target rotational direction is a CW direction, so that 1 is added to a reverse count.

Additionally, in a case where a determination condition at step S107 is not satisfied (step S107, No), that is, a rotational direction of the motor 11 is a CCW direction that is equal to a target rotational direction, the measurement unit 41 determines whether or not a reverse count is more than 0 (step S109). Herein, in a case where a reverse count is more than 0 (step S109, Yes), 1 is subtracted from a reverse count (step S110) and such a process is ended, or otherwise (step S109, No), such a process is ended with no change.

Moreover, in a case where a determination condition at step S101 is not satisfied (step S101, No), the measurement unit 41 determines whether or not a current value of an A-phase encoder signal is not equal to a value of the A-phase encoder signal at a time of a previous process (step S111).

Subsequently, the measurement unit 41 determines whether or not a target rotational direction is not a CW direction based on the target rotational direction information 51 (step S112) in a case where a current value of an A-phase encoder signal is not equal to a value of the A-phase encoder signal at a time of a previous process (step S111, Yes). Then, in a case where a target rotational direction is not a CW direction (step S112, Yes), 1 is added to a reverse count (step S113) and such a process is ended.

That is, in a case of "step S101, No" and "step S111, Yes", a rotational direction of the motor 11 is a CW direction as illustrated in FIG. 11. Then, in a case of "step S112, Yes", a target rotational direction is a CCW direction, so that 1 is added to a reverse count.

Additionally, in a case where a determination condition at step S112 is not satisfied (step S112, No), that is, in a case where a rotational direction of the motor 11 is a CW direction that is equal to a target rotational direction, the measurement unit 41 determines whether or not a reverse count is more than 0 (step S114). Herein, in a case where a reverse count is more than 0 (step S114, Yes), 1 is subtracted from the reverse count (step S115) and such a process is ended, or otherwise (step S114, No), such a process is ended with no change.

Furthermore, in a case where a determination condition at step S111 is not satisfied (step S111, No), the measurement unit 41 determines whether or not a target rotational direction is not a CCW direction based on the target rotational direction information 51 (step S116). Then, in a case where a target rotational direction is not a CCW direction (step S116, Yes), 1 is added to a reverse count (step S117) and such a process is ended.

That is, in a case of "step S101, No" and "step S111, No", a rotational direction of the motor 11 is a CCW direction as illustrated in FIG. 11. Then, in a case of "step S116, Yes", a target rotational direction is a CW direction, so that 1 is added to a reverse count.

Additionally, in a case where a determination condition at step S116 is not satisfied (step S116, No), that is, in a case where a rotational direction of the motor 11 is a CCW direction that is equal to a target rotational direction, the measurement unit 41 determines whether or not a reverse count is more than 0 (step S118). Herein, in a case where a reverse count is more than 0 (step S118, Yes), 1 is subtracted from a reverse count (step S119) and such a process is ended, or otherwise (step S118, No) such a process is ended with no change.

Thus, a reverse count is measured based on an encoder signal that is output from the encoder 14 that has a resolution that is higher than that of the hall element 15, so that it is possible to detect reversal of the motor 11 quickly after the motor 11 is reversed.

Figure 12:
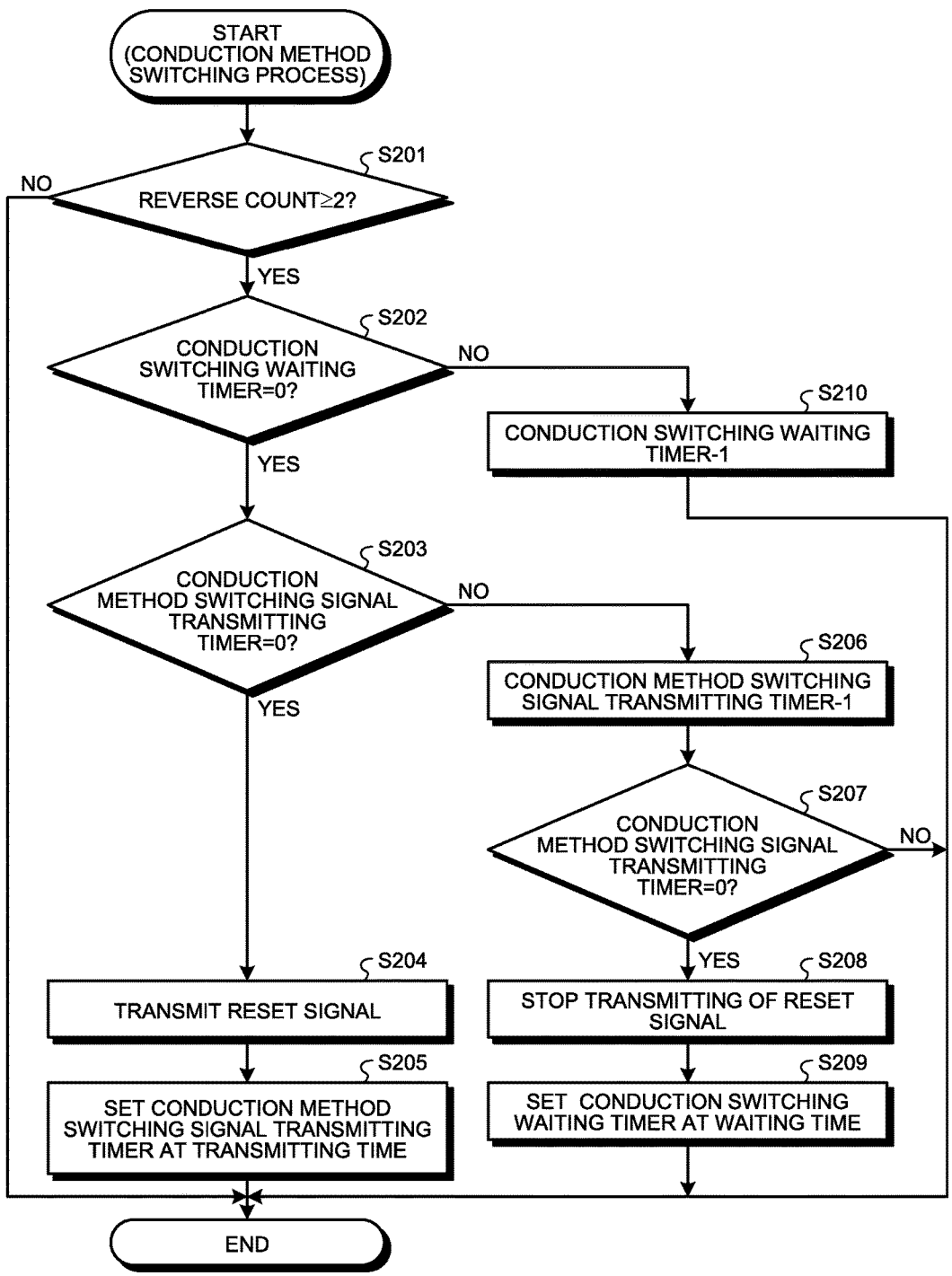
FIG. 12 is a flowchart illustrating a transmission process for a reset signal according to an embodiment.

FIG. 12 is a flowchart illustrating a switching process for a conduction method (a transmission process for a reset signal) according to an embodiment. Additionally, a transmission process for a reset signal as illustrated in FIG. 12 is executed at each predetermined time interval (for example, 500 (μs)).

As illustrated in FIG. 12, the transmitting unit 42 first determines whether or not a reverse count is 2 or more (that is, a count threshold or more) (step S201), and in a case where the reverse count is 2 or more (step S201, Yes), whether or not a value of a conduction switching waiting timer is "0" is determined (step S202). Additionally, in a case where a determination condition at step S201 is not satisfied (step S201, No), such a process is ended.

Subsequently, in a case where a value of a conduction switching waiting timer is "0" (step S202, Yes), the transmitting unit 42 determines whether or not a value of a conduction method switching signal transmitting timer is "0" (step S203). Then, in a case where a value of a conduction method switching signal transmitting timer is "0" (step S203, Yes), the transmitting unit 42 transmits a reset signal to the motor driver 13 (step S204), and sets the conduction method switching signal transmitting timer at a transmitting time of a reset signal (step S205), and such a process is ended.

Additionally, in a case where a determination condition at step S203 is not satisfied (step S203, No), the transmitting unit 42 subtracts 1 from a value of a conduction method switching signal transmitting timer (step S206) and determines whether or not a value of the conduction method switching signal transmitting timer is "0" (step S207).

Then, in a case where a value of a conduction method switching signal transmitting timer is "0" (step S207, Yes), the transmitting unit 42 stops transmitting of a reset signal (step S208), and sets a conduction switching waiting timer at a waiting time for once waiting transmitting of a reset signal (step S209), and such a process is ended. Additionally, in a case where a determination condition at step S207 is not satisfied (step S207, No), such a process is ended with no change.

Furthermore, in a case where a determination condition at step S202 is not satisfied (step S202, No), the transmitting unit 42 subtracts 1 from a value of a conduction switching waiting timer (step S210) and such a process is ended.

In a case where a reverse count is continuously 2 or more (that is, a count threshold or more) due to a transmission process for a conduction method switching signal as already described, it is possible for the transmitting unit 42 to transmit a conduction method switching signal for a predetermined on-time (that corresponds to a conduction switching signal transmitting timer), subsequently stops transmitting for a predetermined off-time (that corresponds to a conduction switching waiting timer), and subsequently repeat a process that transmits a conduction method switching signal for a predetermined on-time again.

That is, in a case where the transmitting unit 42 transmits a conduction method switching signal to the motor driver 13 and subsequently a reverse count is continuously a count threshold or more, it is possible to transmit such a conduction method switching signal to the motor driver 13 intermittently (regularly).

Therefore, according to an embodiment, even if the motor driver 13 is not restarted by a single transmission of a conduction method switching signal, such a conduction method switching signal is repeatedly transmitted, so that it is possible to restart the motor driver 13 reliably.

Moreover, according to an embodiment, even if the motor driver 13 is not restarted by a single transmission of a conduction method switching signal, transmitting is stopped for a predetermined off-time and transmitting is executed again, so that it is possible to restart the motor driver 13 more reliably.

As described above, according to an embodiment, in a case where a reverse count is measured based on an encoder signal from the encoder 14 and such a reverse count is a predetermined count threshold or more, the motor driver 13 is forcibly restarted, so that it is possible to drive the motor 11 continuously even in a case where the motor 11 is reversed by an external factor before a conduction method is switched from the 180-degree conduction method to the 120-degree conduction method.

Additionally, although a case where the speed command signal generator 100 and the rotational direction signal generator 110 are external devices has been described in the embodiment as described above, at least one of the speed command signal generator 100 and the rotational direction signal generator 110 may be placed in an interior of the motor device 10 as a motor drive controlling apparatus.

Furthermore, a case where the motor 11 is a brushless DC motor has been described in the embodiment as described above. However, a position detector (encoder 14) that outputs a pulsed signal dependent on a clock signal is arranged and it is possible to apply a motor drive controlling method as described in an embodiment to a motor capable of rotational speed control that is executed by a clock signal.

Furthermore, although the blood pump 1 that pumps blood in the tube 2 has been described as an example of a tube pump in the embodiment as described above, it is also possible to apply a motor drive controlling method as described in an embodiment to, for example, a tube pump that pumps physiological saline or any other liquid.

Furthermore, an example has been described in the embodiment as described above in such a manner that the encoder 14 is used as a position detector and the hall element 15 is used as a magnetic sensor. However, a position detector is not limited to an encoder and a magnetic sensor is also not limited to a hall element. Any combination of a position detector and a magnetic sensor is allowed as long as a resolution of such a position detector is higher than a resolution of such a magnetic sensor.

As described above, a motor drive controlling apparatus according to an embodiment includes the controller 12 that generates and outputs a drive control signal in response to input of a speed command signal and a rotational direction signal, the motor driver 13 that generates a drive signal and outputs the generated drive signal to the motor 11, in response to input of a drive control signal, and the position detector (encoder 14) that detects a rotational position of the motor 11 and outputs a detection signal (encoder signal) that is based on such a detection result. Furthermore, the motor driver 13 provides 120-degree conduction as a conduction method from a start of rotation of the motor 11 to a predetermined rotational speed or provides 180-degree conduction as a conduction method for a predetermined rotational speed or more. Then, the controller 12 has the measurement unit 41 that detects, based on a detection signal (encoder signal), a time point when rotation of the motor 11 is switched to a reverse direction of a target rotational direction that is based on a rotational direction signal by an external factor during input of a speed command signal, and measures a movement amount in a reverse direction from a rotational position of the motor 11 at a time of switching, based on a detection signal (encoder signal), and the transmitting unit 42 that transmits, to the motor driver 13, a switching signal (conduction method switching signal) that switches a conduction method for the motor driver 13 from 180-degree conduction to 120-degree conduction in a case where the movement amount is a predetermined threshold or more. Thereby, it is possible to drive the motor 11 continuously even in a case where the motor 11 is reversed by an external factor before a conduction method is switched from a 180-degree conduction method to the 120-degree conduction method.

Furthermore, in a motor drive controlling apparatus according to an embodiment, the transmitting unit 42 transmits a switching signal (conduction method switching signal) to the motor driver 13 intermittently in a case where the measurement unit 41 detects that the motor 11 rotates in a reverse direction due to an external factor after a switching signal (conduction method switching signal) is transmitted to the motor driver 13. Thereby, it is possible to restart the motor driver 13 reliably.

Furthermore, in a motor drive controlling apparatus according to an embodiment, the transmitting unit 42 stops transmitting of a switching signal (conduction method switching signal) in a case where the measurement unit 41 detects that the motor 11 returns to a target rotational direction. Thereby, it is possible to prevent the motor driver 13 from being unnecessarily restarted in a case where a reverse phenomenon of the motor 11 is removed.

Furthermore, in a motor drive controlling apparatus according to an embodiment, the measurement unit 41 counts a count value (reverse count) that corresponds to a movement amount and the transmitting unit 42 transmits a switching signal (conduction method switching signal) to the motor driver 13 in a case where such a count value (reverse count) is a specified value (count threshold). Thereby, a count threshold is set at "2", so that it is possible to avoid determining a chattering phenomenon where, as the motor 11 rotates at an extremely low speed, a rotational direction fluctuates, to be reverse rotation that is caused by an external factor.

Furthermore, a motor drive controlling apparatus according to an embodiment further includes a magnetic sensor (hall element) that detects a position of a magnetic pole for conduction switching of the motor 11 and outputs a positional signal (hall signal) that is based on a result of such detection. Furthermore, the motor driver 13 executes a protective operation that stops generation of a drive signal in a case where detection is executed based on a positional signal (hall signal) in such a manner that the motor 11 starts rotation in a reverse direction due to an external factor. Then, the transmitting unit 42 transmits a switching signal (conduction method switching signal) to the motor driver 13 before detection is executed based on a positional signal (hall signal) in such a manner that the motor 11 starts rotation in a reverse direction in a case where the motor 11 starts rotation in a reverse direction due to an external factor. Thereby, it is possible to prevent the motor 11 from starting a protective operation even in a case where the motor 11 is reversed by an external factor before a conduction method is switched from a 180-degree conduction method to a 120-degree conduction method.

Furthermore, in a motor drive controlling apparatus according to an embodiment, a resolution of a position detector (encoder 14) is higher than a resolution of a magnetic sensor (hall element). Thereby, it is possible for the controller 12 to detect rotation of the motor 11 in a reverse direction quickly based on an encoder signal from the encoder 14 before the motor driver 13 starts a protective operation based on a hall signal from the hall element 15.

Furthermore, a tube pump according to an embodiment includes the motor 11, the rollers 34a, 34b that are rotated by drive of the motor 11, and press the tube 2 to deliver liquid contained in the tube 2, and a motor drive controlling apparatus that executes a motor drive controlling method as described above. Thereby, it is possible to drive the motor 11 continuously even in a case where the motor 11 is reversed by an external factor before a conduction method is switched from a 180-degree conduction method to a 120-degree conduction method, so that it is possible to improve reliability of a tube pump.

According to an aspect of the present invention, it is possible to drive a motor continuously even in a case where such a motor is reversed by an external factor.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A motor drive controlling apparatus, comprising:
    a controller that generates and outputs a drive control signal in response to an input of a speed command signal and a rotational direction signal;
    a motor driver that generates a drive signal and outputs the generated drive signal to a motor, in response to an input of the drive control signal; and
    a position detector that detects a rotational position of the motor and outputs a detection signal that is based on a detection result, wherein
    the motor driver provides 120-degree conduction as a conduction method from a start of rotation of the motor to a predetermined rotational speed or provides 180-degree conduction as a conduction method for the predetermined rotational speed or more, and
    the controller has
    a measurement unit that detects a time point when rotation of the motor is switched to a reverse direction of a target rotational direction that is based on the rotational direction signal by an external factor during input of the speed command signal, based on the detection signal, and measures a movement amount in the reverse direction from a rotational position of the motor at a time point of the switching, based on the detection signal, and
    a transmitting unit that transmits, to the motor driver, a switching signal that switches a conduction method for the motor driver from the 180-degree conduction to the 120-degree conduction in a case where the movement amount is a predetermined threshold or more.

2. The motor drive controlling apparatus according to claim 1, wherein
    the transmitting unit transmits the switching signal to the motor driver intermittently in a case where the measurement unit detects that the motor rotates in the reverse direction due to an external factor after the switching signal is transmitted to the motor driver.

3. The motor drive controlling apparatus according to claim 1, wherein
    the transmitting unit stops transmitting of the switching signal in a case where the measurement unit detects that the motor returns to the target rotational direction.

4. The motor drive controlling apparatus according to claim 1, wherein
    the measurement unit counts a count value that corresponds to the movement amount, and
    the transmitting unit transmits the switching signal to the motor driver in a case where the count value is a specified value.

5. The motor drive controlling apparatus according to claim 1, further comprising
    a magnetic sensor that detects a position of a magnetic pole for conduction switching of the motor and outputs a positional signal that is based on a detection result, wherein
    the motor driver executes a protective operation that stops generation of the drive signal in a case where detection is executed based on the positional signal in such a manner that the motor starts rotation in the reverse direction due to an external factor, and
    the transmitting unit transmits the switching signal to the motor driver before detection is executed based on the positional signal in such a manner that the motor starts rotation in the reverse direction in a case where the motor starts rotation in the reverse direction due to an external factor.

6. The motor drive controlling apparatus according to claim 5, wherein a resolution of the position detector is higher than a resolution of the magnetic sensor.

7. A motor drive controlling method that executes control in such a manner that a motor driver that generates, and outputs to a motor, a drive signal provides 120-degree conduction as a conduction method from a start of rotation of the motor to a predetermined rotational speed or provides 180-degree conduction as a conduction method for the predetermined rotational speed or more, comprising:
   a measurement step that detects a time point when rotation of the motor is switched to a reverse direction of a target rotational direction that is based on a rotational direction signal by an external factor during input of a speed command signal, based on a detection signal that is output from a position detector that detects a rotational position of the motor, and measures a movement amount in the reverse direction from a rotational position of the motor at a time point of the switching, based on the detection signal, and
   a transmission step that transmits, to the motor driver, a switching signal that switches a conduction method for the motor driver from the 180-degree conduction to the 120-degree conduction in a case where the movement amount is a predetermined threshold or more.

8. A tube pump, comprising:
   a motor;
   one or more rollers that are rotated by drive of the motor, and press a tube to deliver liquid contained in the tube;
   a motor drive controlling apparatus including:
      a controller that generates and outputs a drive control signal, in response to an input of a speed command signal and a rotational direction signal;
      a motor driver that generates a drive signal and outputs the generated drive signal to a motor, in response to an input of the drive control signal; and
      a position detector that detects a rotational position of the motor and outputs a detection signal that is based on a detection result, wherein
   the motor driver provides 120-degree conduction as a conduction method from a start of rotation of the motor to a predetermined rotational speed or provides 180-degree conduction as a conduction method for the predetermined rotational speed or more, and
   the controller has
   a measurement unit that detects a time point when rotation of the motor is switched to a reverse direction of a target rotational direction that is based on the rotational direction signal by an external factor during input of the speed command signal, based on the detection signal, and measures a movement amount in the reverse direction from a rotational position of the motor at a time point of the switching, based on the detection signal, and
   a transmitting unit that transmits, to the motor driver, a switching signal that switches a conduction method for the motor driver from the 180-degree conduction to the 120-degree conduction in a case where the movement amount is a predetermined threshold or more.

* * * * *